United States Patent
Omura et al.

[11] Patent Number: 5,807,721
[45] Date of Patent: Sep. 15, 1998

[54] COMPOUND FO-1289, PROCESS OF PRODUCTION WITH ASPERGILLUS AND STRAIN

[75] Inventors: Satoshi Omura; Hiroshi Tomoda; Rokuro Masuma, all of Tokyo, Japan

[73] Assignee: The Kitasato Institute, Tokyo, Japan

[21] Appl. No.: 567,066

[22] Filed: Dec. 4, 1995

Related U.S. Application Data

[63] Continuation of Ser. No. 256,776, filed as PCT/JP93/00364, Mar. 23, 1993 published as WO94/09147, Apr. 28, 1994, abandoned.

[30] Foreign Application Priority Data

Oct. 22, 1992  [JP]  Japan ..................................... 4-284759
Feb. 24, 1993  [JP]  Japan ..................................... 5-035261

[51] Int. Cl.⁶ ............................... C12P 17/18; C12N 1/14
[52] U.S. Cl. ...................... 435/119; 435/254.1; 435/913; 435/256.1; 546/270
[58] Field of Search ................................. 435/119, 156.1, 435/254.1, 913; 546/270

[56] References Cited

U.S. PATENT DOCUMENTS

| | | | |
|---|---|---|---|
| 4,231,938 | 11/1980 | Monaghan | 260/943.5 |
| 5,151,365 | 9/1992 | Dombrowski | 435/242 |
| 5,250,935 | 10/1993 | Cover | 435/256.1 |

FOREIGN PATENT DOCUMENTS 360895  12/1992  Japan .

OTHER PUBLICATIONS

"Manufacture of FO–1284 Substance from Aspergillus sp. FO–1289 as Acyl–Coenzyme A : Cholesterol Acyltransferas (ACAT) Inhibitor", Chemical Abstracts, vol. 118, No. 24, Jun. 14, 1993, Columbus, Ohio, Abstract No. 24093b, p. 481, by Satoshi Omura et al.

*Primary Examiner*—Irene Marx
*Attorney, Agent, or Firm*—Young & Thompson

[57] ABSTRACT

A FO-1289 substance of the formula

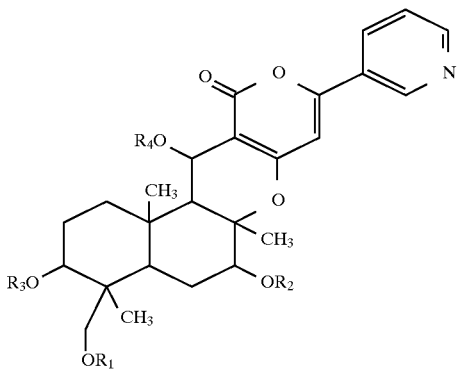

wherein $R_1$, $R_2$, $R_3$ and $R_4$ are hydrogen or acyl. A process for the production thereof comprises culturing the novel microorganism Aspergillus sp. FO-1289 FERM BP-4242 in a nutrient medium, accumulating the FO-1289 substance thus produced in the medium, and isolating the FO-1289 substance therefrom. Particular species of the FO-1289 substance comprise FO-1289A, in which $R_1$, $R_2$ and $R_3$ are acetyl and $R_4$ is hydrogen; FO-1289B, wherein $R_1$ is propionyl, $R_2$ and $R_3$ are acetyl and $R_4$ is hydrogen; FO-1289C, wherein $R_1$ and $R_3$ are acetyl, $R_2$ is propionyl and $R_4$ is hydrogen; and FO-1289D, wherein $R_1$ and $R_2$ are acetyl, $R_3$ is propionyl and $R_4$ is hydrogen.

6 Claims, 16 Drawing Sheets

COMPOUND FO-1289, PROCESS OF PRODUCTION WITH ASPERGILLUS AND STRAIN

This application is a continuation of application Ser. No.08/256,776, filed as PCT/JP93/00367, Mar. 23, 1993 published as WO94/09147, Apr. 28, 1994, now abandoned.

The present invention relates to a novel FO-1289 substance having an inhibitory activity for acylcoenzyme A cholesterol acyltransferase (hereinafter designated as acyl CoA cholesterol acyltransferase).

Heretofore some pharmaceutical products for treatment of hyperlipemia. Among them, a drug having an action on (1) cholesterol synthesis inhibition, (2) cholesterol absorption inhibition, (3) stimulation of cholesterol catabolism and (4) activation of lipoprotein lipase (suppression of lipoprotein synthesis), has been known.

In recent years, the symptoms attributable to accumulation of cholesterol in vivo such as hyperlipemia and arteriosclerosis in adult are becoming a world-wide problems. Hyperlipemia has known as a factor for stimulating a progress of arteriosclerosis, and hence ischemic cardiopathy can be decreased by lowering blood cholesterol level. The crisis of myocardial infarction caused by hyperlipemia is observed at a high rate. Accordingly more effective and safe medicament for treatment of hyperlipemia, in particular hypercholesterolemia, is desirable.

Cholesterol is converted to cholesterol ester by an action of acyltransfer from acyl CoA which is accumulated in the cells and in blood lipoprotein. An enzyme which catalyses acyltransfer reaction is acyl CoA cholesterol acyltransferase, and is specifically related to adsorption of cholesterol from the intestinal tract and a formation of the foam cells in the coronary artery. Therefore acyl CoA cholesterol acyltransferase inhibitor is estimated to be effective for treatment of the hypercholesterolemia. To provide acyl CoA cholesterol acyltransferase inhibitor is expected to be useful for treatment of the diseases of adult people such as hyperlipemia or arteriosclerosis attributed therefrom.

We have found according to a continued studies on the metabolic products produced by microorganisms that substances having an inhibitory activity for acyl CoA cholesterol acyltransferase is produced in a fermentation broth of microorganism strain FO-1289 isolated from soil sample. Further we have isolated the substances having inhibitory activity for acyl CoA cholesterol acyltransferase which have physico-chemical properties described hereinbelow. These substances are novel compounds and were given a general name FO-1289 substance.

An object of the present invention is to provide FO-1289 substance.

Another object of the present invention is to provide FO-1289A substance of the molecular formula $C_{31}H_{37}NO_{10}$, and FO-1289B substance. FO-1289C substance and FO-1289D substance, the latter three of which having molecular formula $C_{32}H_{39}NO_{10}$.

The isolated compounds from fermentation broth may chemically be modified by means of the standard method known in the art. For example, in order to prepare acylated compounds, the isolated compounds are treated with an acylating agent in an adequate solvent at an ambient temperature through to reflux temperature.

Further object of the present invention is to provide a process for production of FO-1289 substance which comprise producing the FO-1289 substances by culturing microorganism belonging to genus Aspergillus in a nutrient medium, accumulating the FO-1289 substance therein, and isolating the FO-1289 substance therefrom.

More further object of the present invention is to provide a microorganism strain belonging to genus Aspergillus having an ability to produce FO-1289 substance.

The microorganism having an ability to produce FO-1289 substance (FO-1289 substance producing microorganism) belongs to genus Aspergillus. For example a microorganism strain FO-1289 belonging to genus Aspergillus isolated by the inventors of the present invention is one of the most preferable strain used in the process of the present invention.

Taxonomical properties of the strain FO-1289 are shown in the followings.

TAXONOMICAL PROPERTIES

I. The strain FO-1289 shows good growth on a malt extract agar medium, Czapek-yeast extract agar medium and 20% sucrose -Czapek-yeast extract agar medium with good formation of conidia. Microscopical observation of colony grown on Czapek-yeast extract agar medium shows conidiophores mainly grown directly from substrate mycelia with smooth surface. The edge of conidiophores is a swelling with ampulli-form vesicles (diameter 10–25 μm). No formation of metulae. Phialide is formed directly on the vesicle. Diameter of conidia is 2–3 μm with spherical or subspherical form.

II. OBSERVATION ON VARIOUS MEDIA (1) Cultural observations of the strain are illustrated in Table 1. Observations were taken macroscopically after cultivation at 25° C. for 7 days.

TABLE 1

| Medium | Growth appearance (Diameter of colony: mm) | Color of colony Surface | Reverse | Soluble pigment |
|---|---|---|---|---|
| Malt extract agar | Good ( 55 ) Cottony-wooly thin flat growth Conidia: slightly dence formation | Pale yellow-ish white | Pale yellow-ish white | None |
| Czapek-yeast extract agar | Good ( >60 ) Velvety growth Conidia: dence formation | Blueish green | Pale yellow | None |
| 20% sucrose-Czapek-yeast extract agar | Good ( 55 ) Velvety growth Conidia: dence formation | Blueish green | Pale olive | None |

(2) Growth appearance on Czapek-yeast extract agar medium at 37° C. for 7 days culture is abundant (over 80 mm). No growth is observed at 5° C. for 7 days culture. No formation of exudate and sclerotia accompanied with growth of microorganism on the all of the medium hereinabove are observed.

III. physiological properties (1) Growth temperature: 15°–47° C.

(2) Optimum growth temperature: 27°–40° C.

(3) Growth pH: 3–11

(4) Optimum growth pH: 5–8

(5) Nature: aerobic

In comparison with the above properties of the strain FO-1289 based upon the morphological properties, various properties on culture and physiological properties, and the taxonomical properties of known microorganism species, the present strain FO-1289 is defined as the strain belonging to genus Aspergillus and is referred to Aspergillus sp. FO-1289. The strain has been deposited in the National Institute of Bioscience and Human-Technology, Agency of Industrial Science and Technology with the deposition No. FERM BP-4242.

Although a description of the strain FO-1289 was given hereinabove, taxonomical properties of the microorganism strain are in general very mutable and are not stable. Spontaneous mutation and artificial mutation with ultraviolet radiation or treatment with mutagen such as N-methyl-N-nitro-N-nitrosoguanidine or ethyl methanesulfonate of microorganisms are well known. Therefore not only artificial but also spontaneous mutants of which belong to genus Aspergillus and have FO-1289 substance producing ability can be usable in the present invention. Further, the mutated strain obtained by cell technology method such as cell fusion and gene manipulation technology which produce can be included within the scope of the FO-1289 substance producing microorganism of the present invention.

Preferable example of the strain used for production of FO-1289 substance of the present invention is Aspergillus sp. FO-1289, FERM BP-4242, isolated from soil sample by the present inventor.

In the present invention, a microorganism FO-1289 substance producing strain belonging to genus Aspergillus is cultured in a nutrient medium. A culturing method generally used for fungi can be used on the present invention. A nutrient medium containing assimilable carbon source, assimilable nitrogen source and, if required together with inorganic salt can be used. Examples of assimilable carbon sources are glucose, sucrose, maltose, dextrin or cellulose etc. are used with or without combination. Examples of assimilable nitrogen sources are organic nitrogen source such as peptone, meat extract, yeast extract, dry yeast, soybean powder, corn steep liquor, cotton seed cake, caseine, soybean protein hydrolysate, amino acid or urea, and inorganic nitrogen sources such as nitrate salt and ammonium salt, and are used with or without combination. If required, inorganic salt such as sodium salt, potassium salt, calcium salt, magnesium salt and phosphate salt, and heavy metallic salt can be added to the medium. Further, trace nutrient element, growth stimulant or precursor can be added in the medium, if required.

Cultivation can be performed at aerobic condition by shaking or agitation. Submerged aeration agitation cultivation is preferable for industrial production. Cultivation can be preferably performed at neutral pH. Cultivation temperature is usually at 20°–37° C., preferably at 24°–30°0 C. FO-1289 substance are accumulated in the medium by culturing for 2–3 days, and when maximum production of the FO-1289 substance are obtained, cultivation can be terminated.

These culturing condition such as medium composition, pH of the medium, culturing temperature, agitation speed and aeration rate can be varied depending upon the microorganism strain used and the atmospheric conditions for obtaining the preferable result. Anti-foaming agent such as silicon oil, vegetable oil or surface active agent can also be used if necessary. The FO-1289 substance are accumulated in mycelia and in the cultured broth. The FO-1289 substance can preferably be isolated from supernatant and mycelia separated by centrifugation of cultured broth.

The FO-1289 substance can be extracted from supernatant with water-immiscible organic solvent such as ethyl acetate, butyl acetate or benzene, and crude FO-1289 substance can be obtained by concentrating of the extract in vacuo. The crude substance is subjected to a known purification process for lipophilic substance, for example, by column chromatography using a carrier such as silica gel or alumina each component of the FO-1289 substance can be isolated.

The FO-1289 substance can also be isolated from mycelial cells by extracting the mycelial with water-miscible organic solvent. The extract is concentrated under reduced pressure and the concentrate is subjected to further extraction with water-immiscible organic solvent such as ethyl acetate, butyl acetate or benzene. The extract which is optionally combined with the extract obtained from cultured filtrate hereinabove explained, can be purified or it can be purified and separated by the same procedure as of the above described to obtain each component of the FO-1289 substance.

IV. PHYSICO-CHEMICAL PROPERTIES

Physico-chemical properties of FO-1289A substance, FO-1289B substance, FO-1289C substance and FO-1289D substance are illustrated in Table 2.

TABLE 2

| Substance | FO-1289A | FO-12879B | FO-1289C | FO-1289D |
|---|---|---|---|---|
| Molecular formula | $C_{31}H_{37}NO_{10}$ | $C_{32}H_{39}NO_{10}$ | $C_{32}H_{39}NO_{10}$ | $C_{32}H_{39}NO_{10}$ |
| High resolution electron impact mass-spectrum | | | | |
| | 583.242356 | 597.25697 | 597.25603. | 597.25701 |
| Fast atom bombardment mass-spectrum | | | | |
| | 584(M + H)⁺ | 598(M + H)⁺ | 598(M + H)⁺ | 598(M + H)⁺ |
| | 606(M + Na)⁺ | 620(M + Na)⁺ | 620(M + Na)⁺ | 620(M + Na)⁺ |
| Optical rotation $[\alpha]_D^{28}$(Cl, CHCl₃) | | | | |
| | +65.8 | +62.0 | +9.4 | +64.5 |
| UV spectrum (methanol, nm) | | | | |
| | FIG. 1 | FIG. 5 | FIG. 9 | FIG. 13 |
| IR spectrum (CCl₄) | | | | |
| | FIG. 2 | FIG. 6 | FIG. 10 | FIG. 14 |
| ¹H—NMR spectrum (in CDCl₃) | | | | |
| | FIG. 3 | FIG. 7 | FIG. 11 | FIG. 15 |
| ¹³C—NMR spectrum (in CDCl₃) | | | | |
| | FIG. 4 | FIG. 8 | FIG. 12 | FIG. 16 |

Solubility in solvent: soluble in methanol, ethanol, acetonitrile, ethyl acetate and benzene insoluble in water Nature of substance: neutral Appearance: yellowish powder Chemical structure:

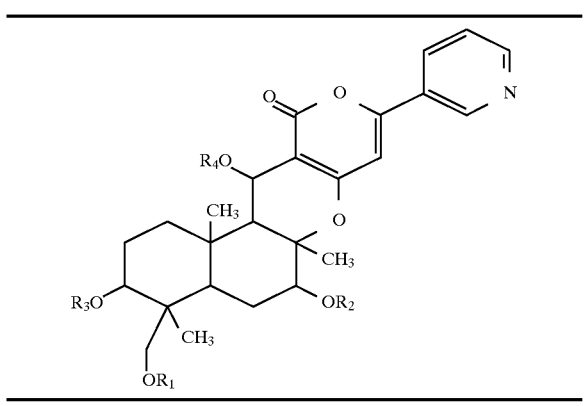

| | | | | |
|---|---|---|---|---|
| FO-1289A | R₁: —CO—CH₃, | | R₂: | —CO—CH₃, |
| substance: | R₃: —CO—CH₃, | | R₄: | —H |
| FO-1289B | R₁: —CO—CH₂—CH₃, | | R₂: | —CO—CH₃, |
| substance: | R₃: —CO—CH₃, | | R₄: | —H |
| FO-1289C | R₁: —CO—CH₃, | | R₂: | —CO—CH₂—CH₃, |
| substance: | R₃: —CO—CH₃, | | R₄: | —H |
| FO-1289D | R₁: —CO—CH₃, | | R₂: | —CO—CH₃, |
| substance: | R₃: —CO—CH₂—CH₃, | | R₄: | —H |

FO- 1289A substance : $R_1$: —CO—CH₃, $R_2$: —CO—CH₃, $R_3$: —CO—CH₃, $R_4$: —H

FO- 1289B substance : $R_1$: —CO—CH₂—CH₃, $R_2$: —CO—CH₃, $R_3$: —CO—CH₃, $R_4$: —H FO- 1289C substance : R: —CO—CH₃, $R_2$: —CO—CH₂—CH₃, $R_3$: —CO—CH₃, $R_4$: —H FO- 1289D substance $R_1$: —CO—CH₃, $R_2$: —CO—CH₃, $R_3$: —CO—CH₂—CH₃, $R_4$: —H

V. BIOLOGICAL PROPERTIES (1) Inhibitory action on rat acyl CoA cholesterol acyltransferase:

An inhibitory action of the FO-1289 substance for acyl CoA cholesterol acyltransferase is tested according to the method of Kyoda et al. (J. Antibiotics, 44: 136 1991). A crude enzyme prepared from rat liver microsome fraction is added in the 100 mM phosphate buffer solution (pH 7.4) 200 $\mu$M containing 300 $\mu$M bovine serum albumin. 30 $\mu$M (1-$^{14}$C) oleoyl-CoA (0.02 $\mu$Ci) and 30 $\mu$M cholesterol (solubilized with 1/30 w/w Triton WR-1339) and incubaatd at 37° C. for 30 minutes. Total lipid is extracted with a mixture of chloroform-methanol (2:1), then each lipid is separated by thin layer chromatography (Kiesel gel GF$_{254}$, developer:petroleum ether—diethyl ether—acetic acid=90:10:1). Radioactivity incorporated in the cholesterol ester fraction is analysed by RI scanner (Ambis Corp.) to assay an activity of acyl CoA cholesterol acyltransferase. The 50% inhibition concentration on the enzyme is shown in Table 3.

TABLE 3

| | FO-1289A | FO-1289B | FO-1289C | FO-1289D |
|---|---|---|---|---|
| IC$_{50}$ ($\mu$M) | 0.04 | 0.1 | 0.03 | 0.15 |

EFFECT OF THE INVENTION

As illustrated hereinabove, FO-1289 substance, and the individual components thereof, of the present invention show strong inhibitory action on acyl CoA cholesterol acyltransferase. Accordingly the substances are useful in the treatment of high serum cholesterol in mammals, including humans. As used herein, treatment is meant to include both the prevention and alleviation of high serum cholesterol. The substances may be administered to a subject in need of treatment by a variety of conventional routes of administration, including oral and parenteral. In general, these substances will be administered orally or parenterally at dosages between about 0.1 and about 10 mg/kg body weight of the subject to be treated per day, preferably from about 0.5 to 5 mg/kg. However, some variation in dosage will necessarily occur depending on the condition of the subject being treated and the activity of the compound being employed. The person responsible for administration will, in any event, determine the appropriate dose for the individual subject.

A substance of the invention may be administered alone or in combination with pharmaceutically acceptable carriers, in either single or multiple doses. Suitable pharmaceutically carriers include inert solid diluents or fillers, sterile aqueous solution and various organic solvents. The resulting pharmaceutical compositions are then readily administered in a variety of dosage forms such as tablets, powders, lozenges, Syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid-compositions of a similar type may also be employed as fillers in sort and hard filled gelatin capsules. Preferred materials for this include lactose or milk sugar and high molecular weight polyethylene glycols. When aqueous suspension's or elixirs are desired for oral administration, the essential active ingredient therein may be combined with various sweetening or flavoring agents coloring matter or dyes and, if desired, emulsifying or suspending agents, together with diluents such as water, ethanol, propylene glycol, glycerin and combinations thereof.

For parenteral administration, solutions of substance of the invention in sesame or peanut oil, aqueous propylene glycol, or in sterile aqueous solution may be employed. Such aqueous solutions should be suitably buffered if necessary and the liquid diluent first rendered isotonic with sufficient saline or glucose. Such solutions are especially suitable for intravenous, intramuscular, subcutaneous and intraperitoneal administration.

Figure 1:
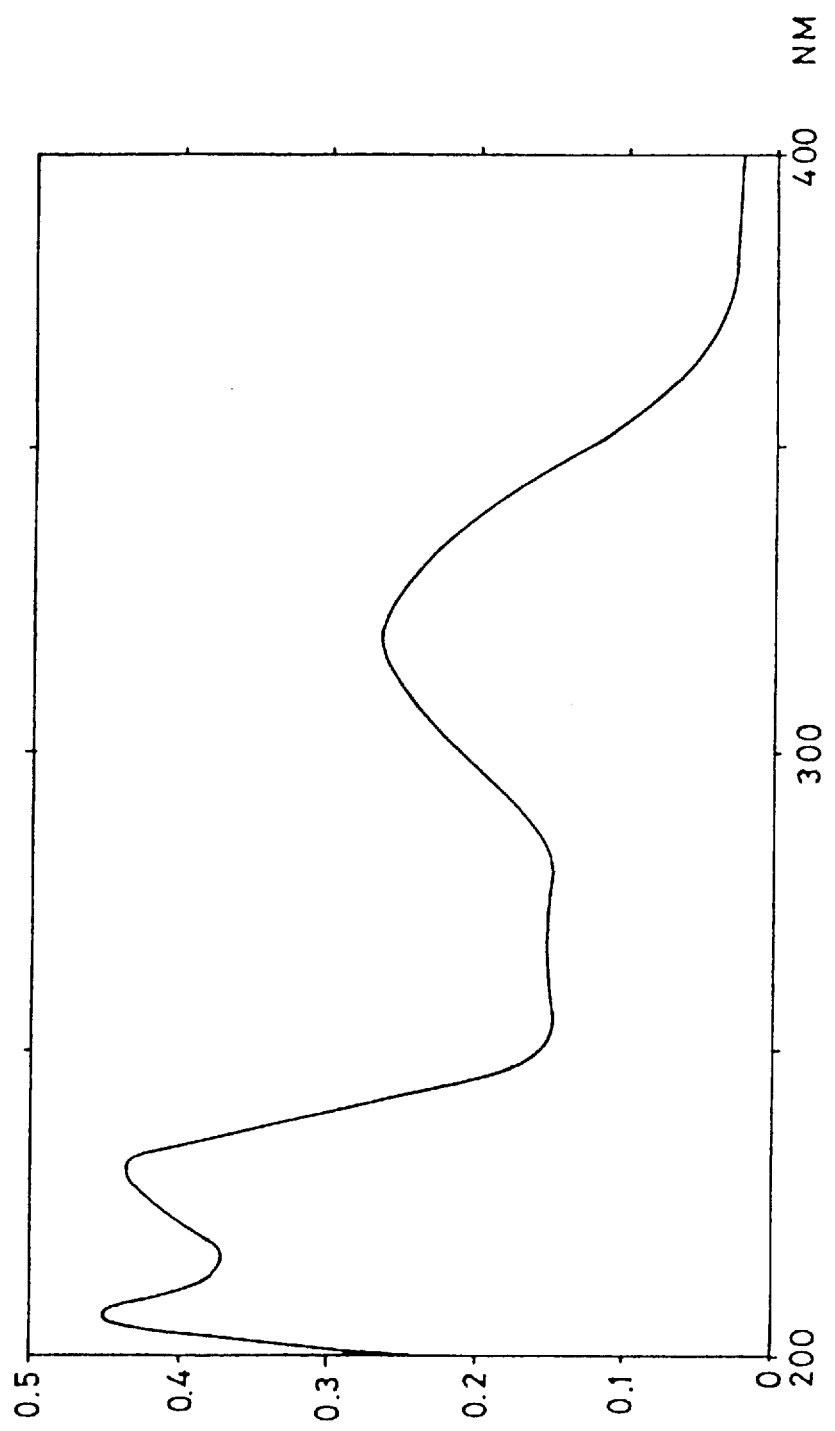
FIG. 1: UV spectrum of FO-1289A substance.
Figure 2:
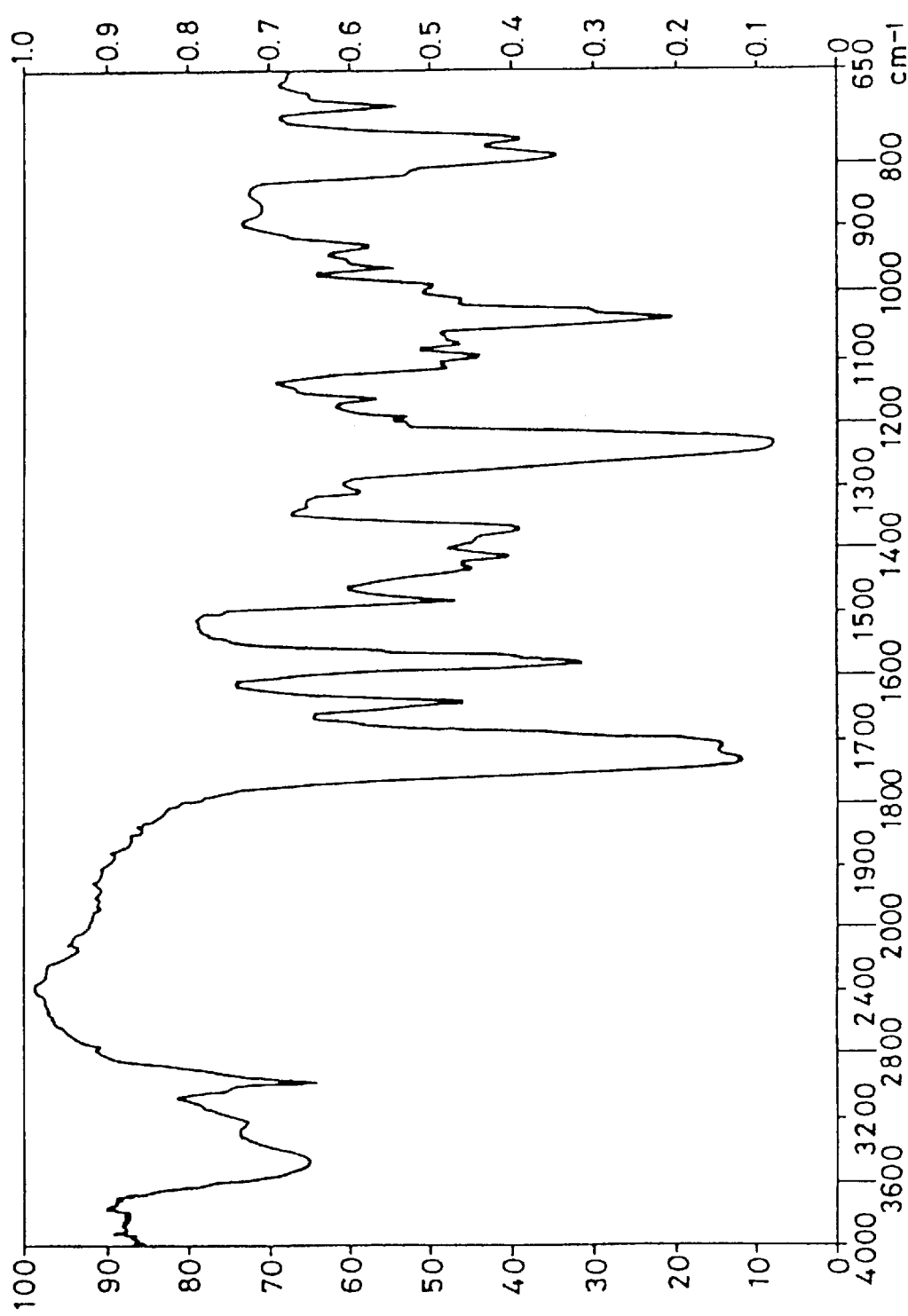
FIG. 2: IR spectrum of FO-1289A substance.
Figure 3:
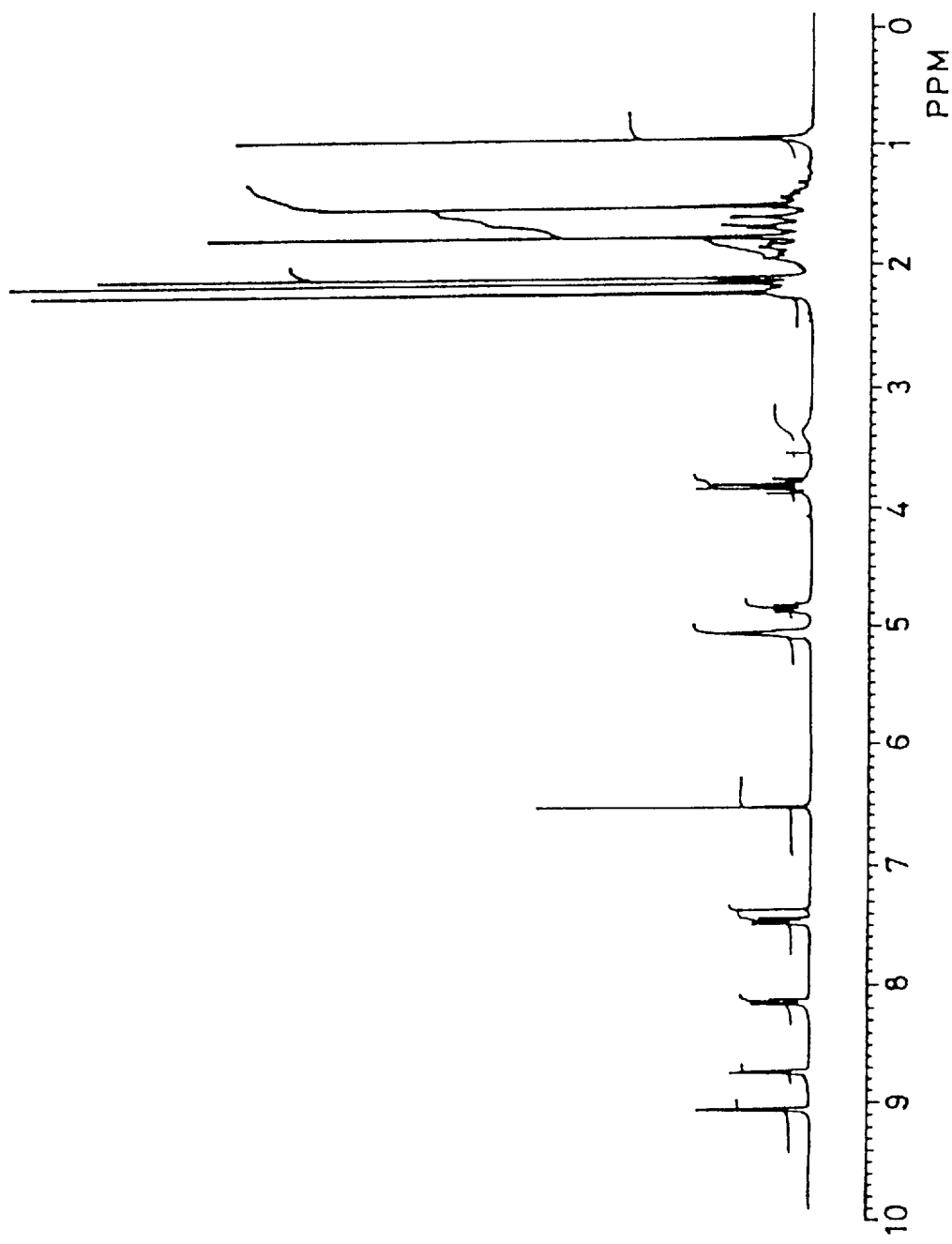
FIG. 3: $^1$H-NHIR spectrum of FO-1289A substance.
Figure 4:
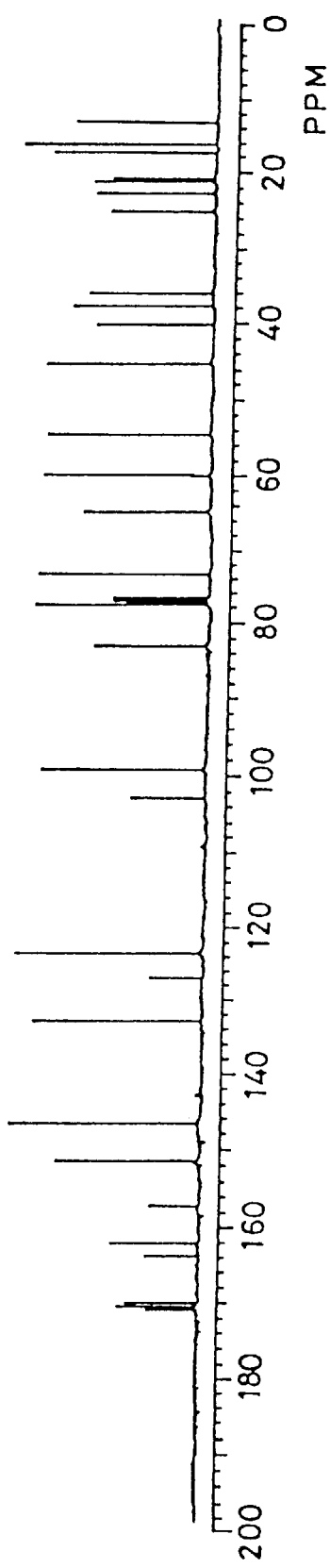
FIG. 4: $^{13}$C-NMR spectrum of FO-1289A substance.
Figure 5:
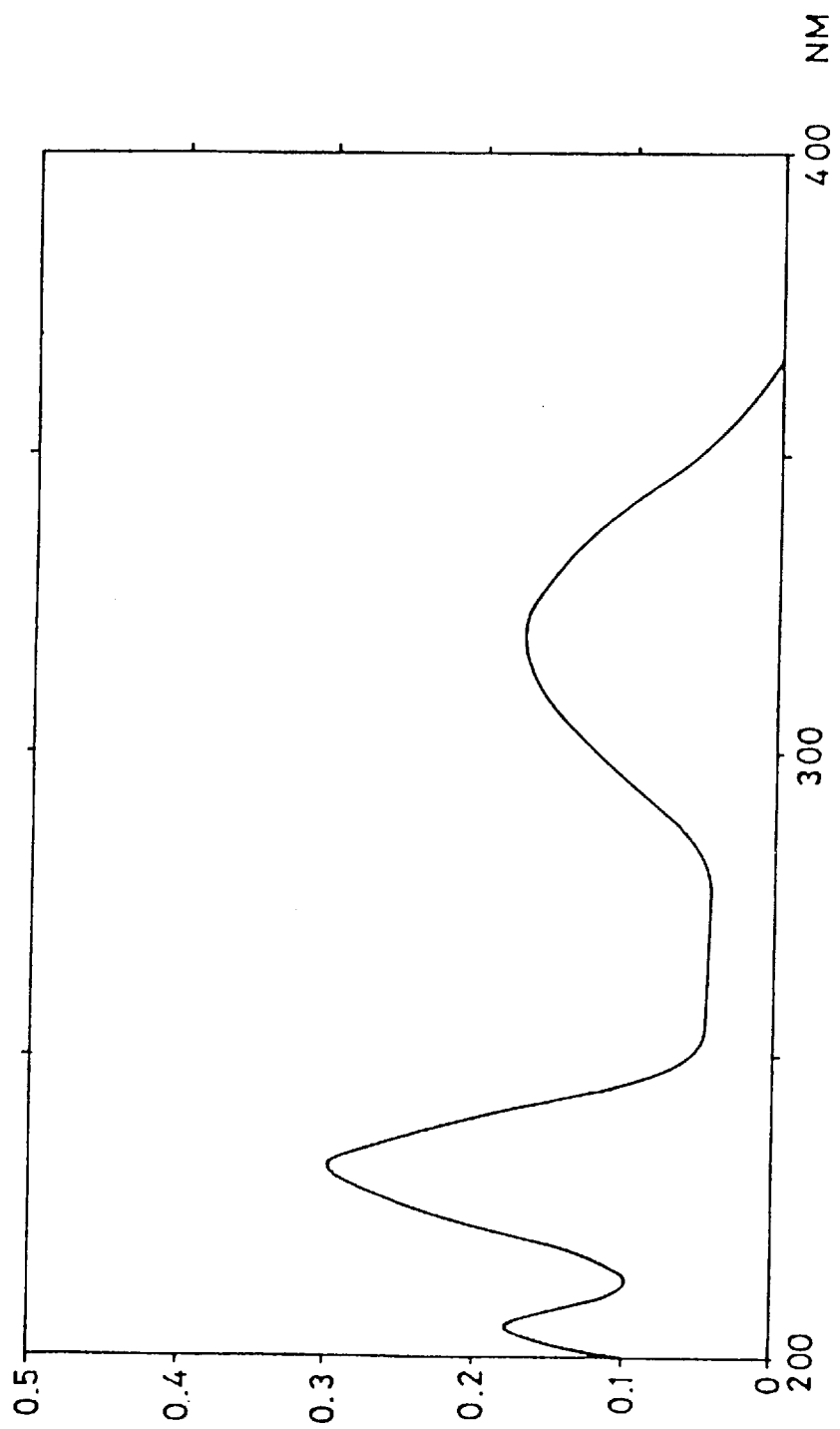
FIG. 5: UV spectrum of FO-1289B substance.
Figure 6:
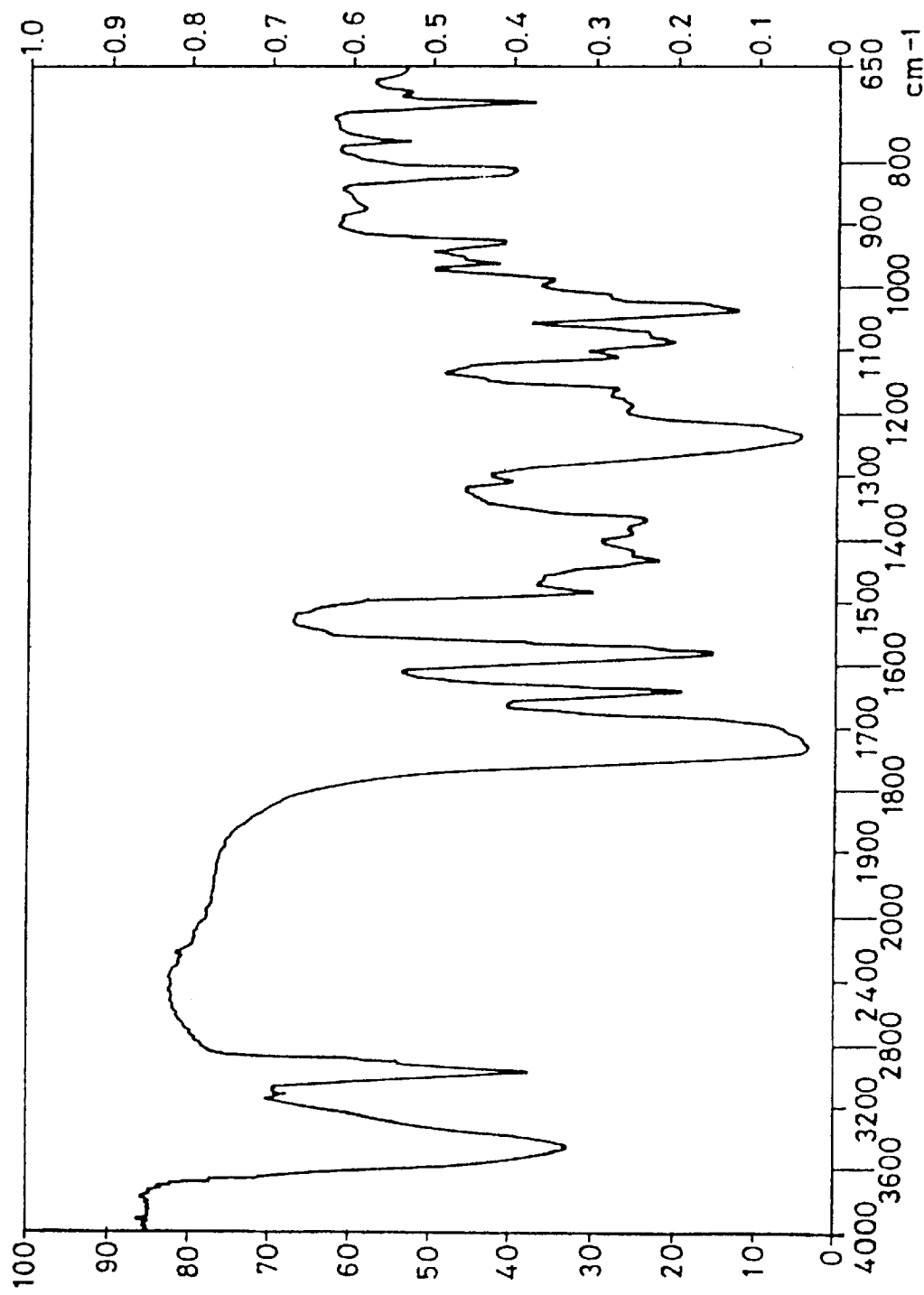
FIG. 6: IR spectrum of FO-1289B substance.
Figure 7:
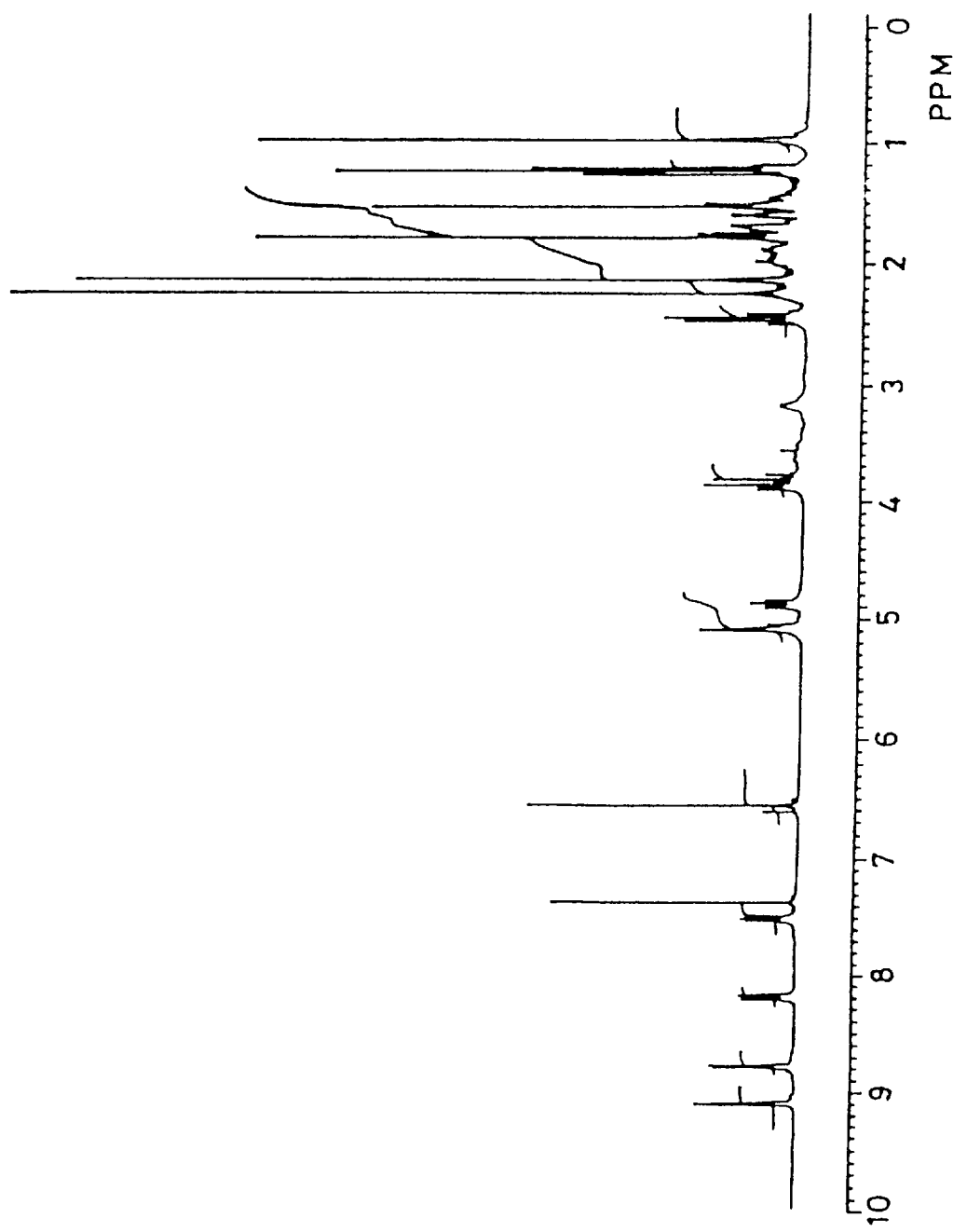
FIG. 7: $^1$H-NMR spectrum of FO-1289B substance.
Figure 8:
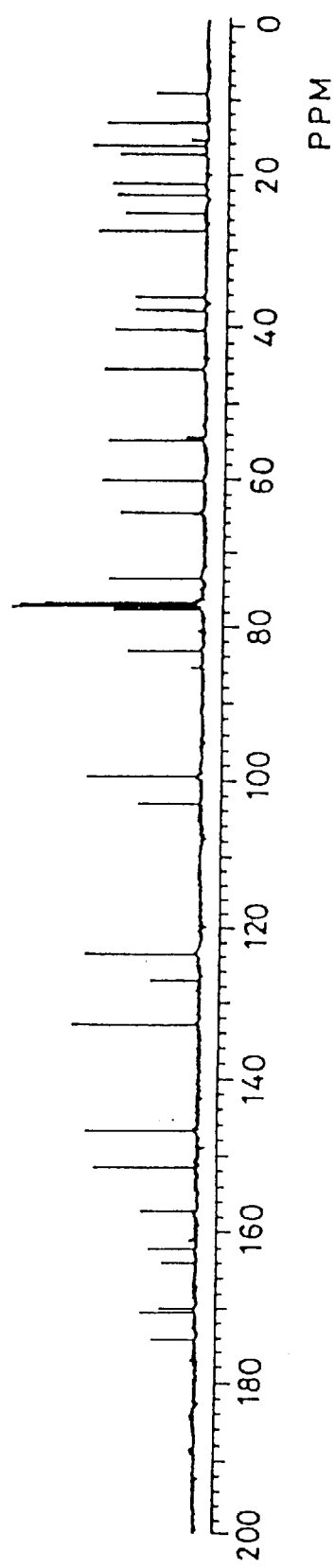
FIG. 8: $^{13}$C-NMR spectrum of FO-1289B substance.
Figure 9:
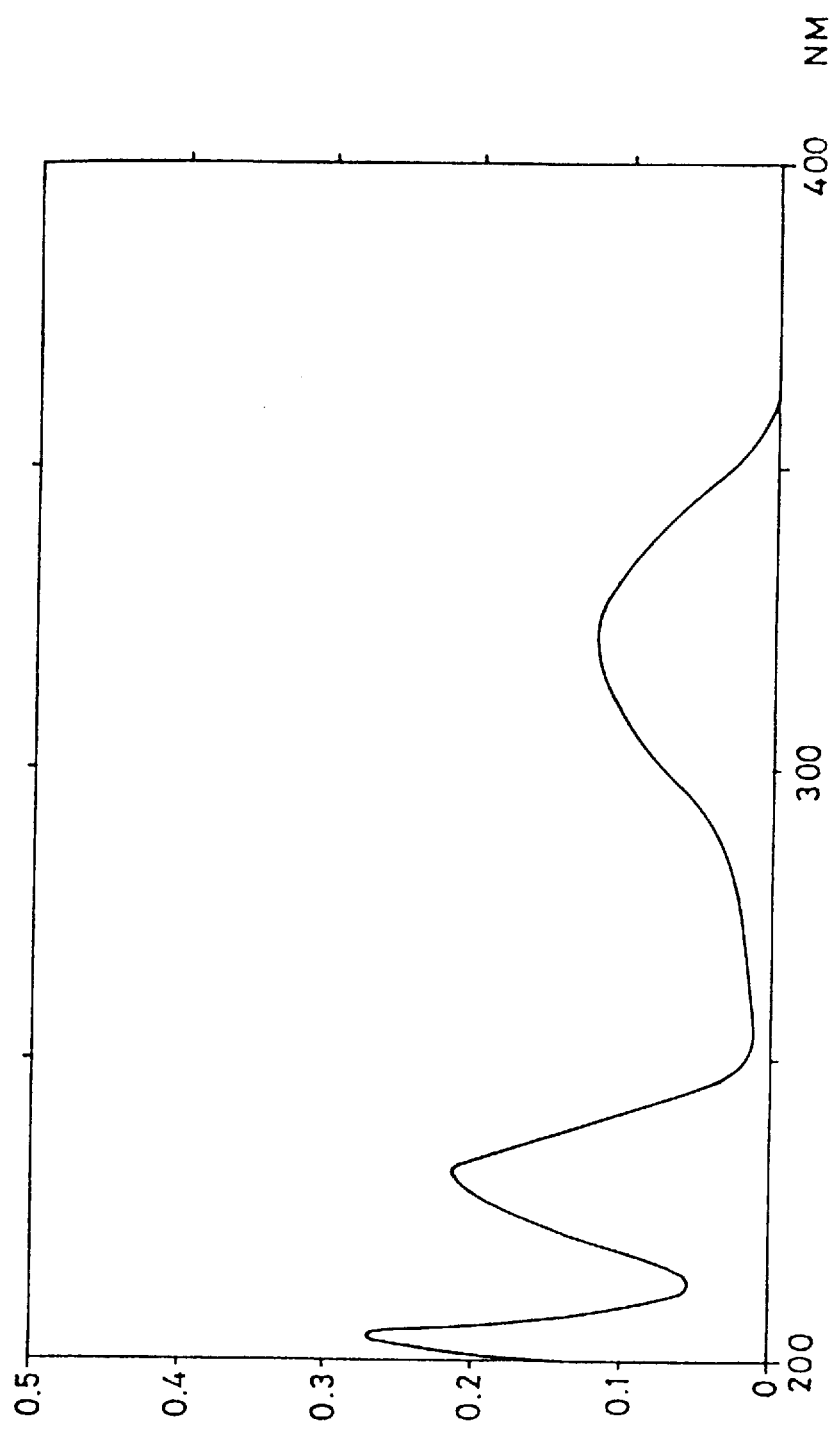
FIG. 9: UV spectrum of FO-1289C substance.
Figure 10:
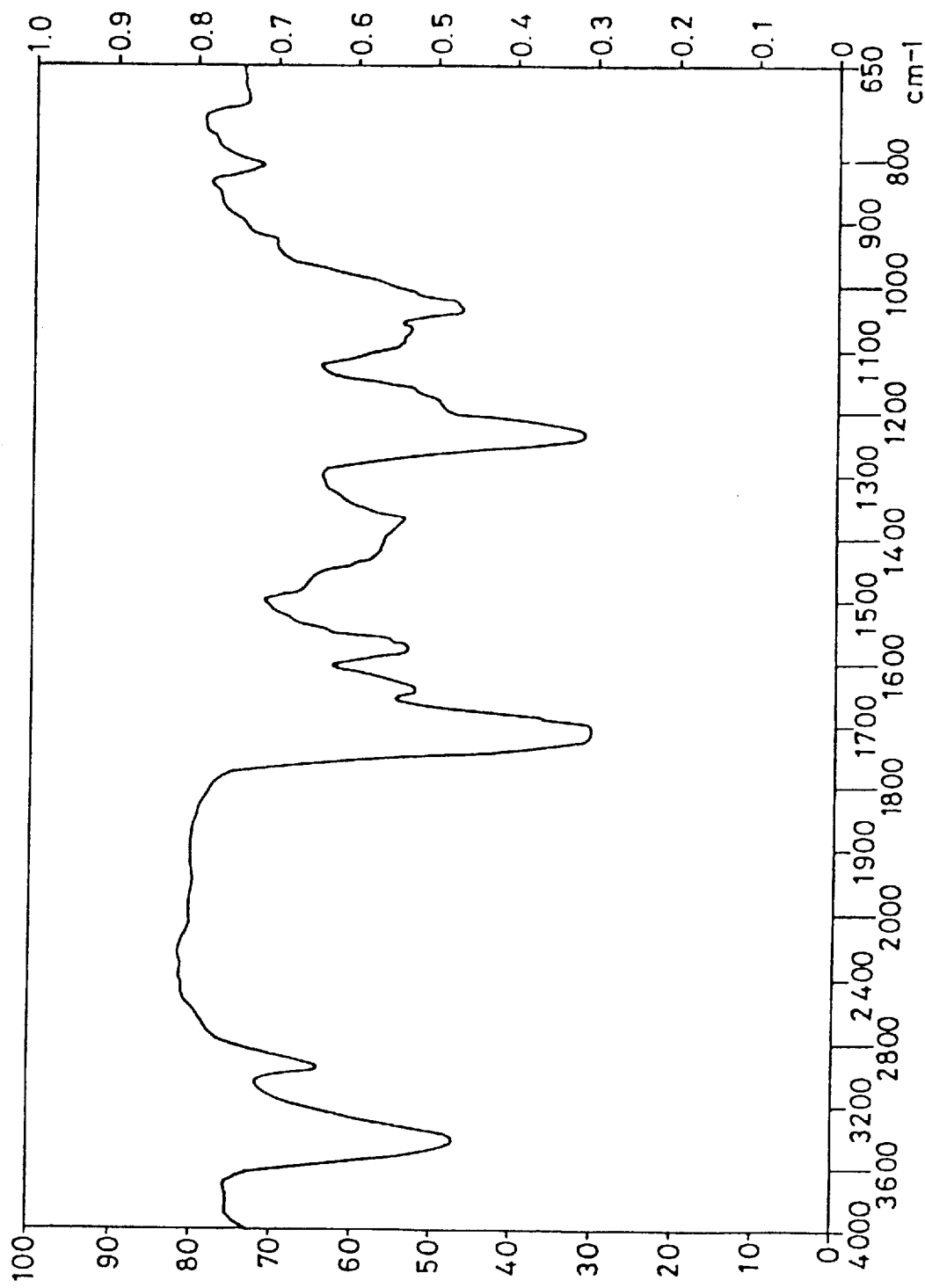
FIG. 10: IR spectrum of FO-1289C substance.
Figure 11:
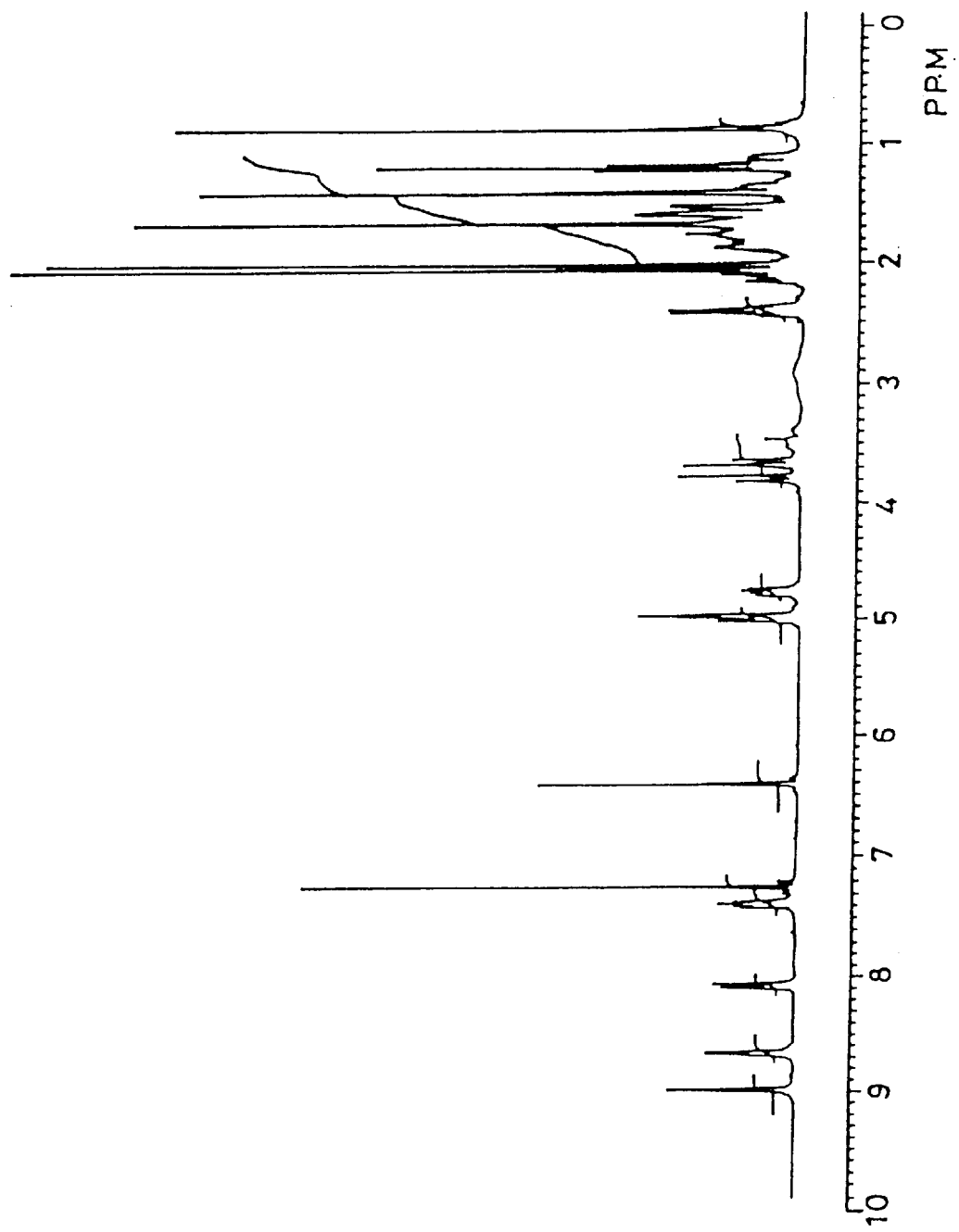
FIG. 11: $^1$H-NMR spectrum of FO-1289C substance.
Figure 12:
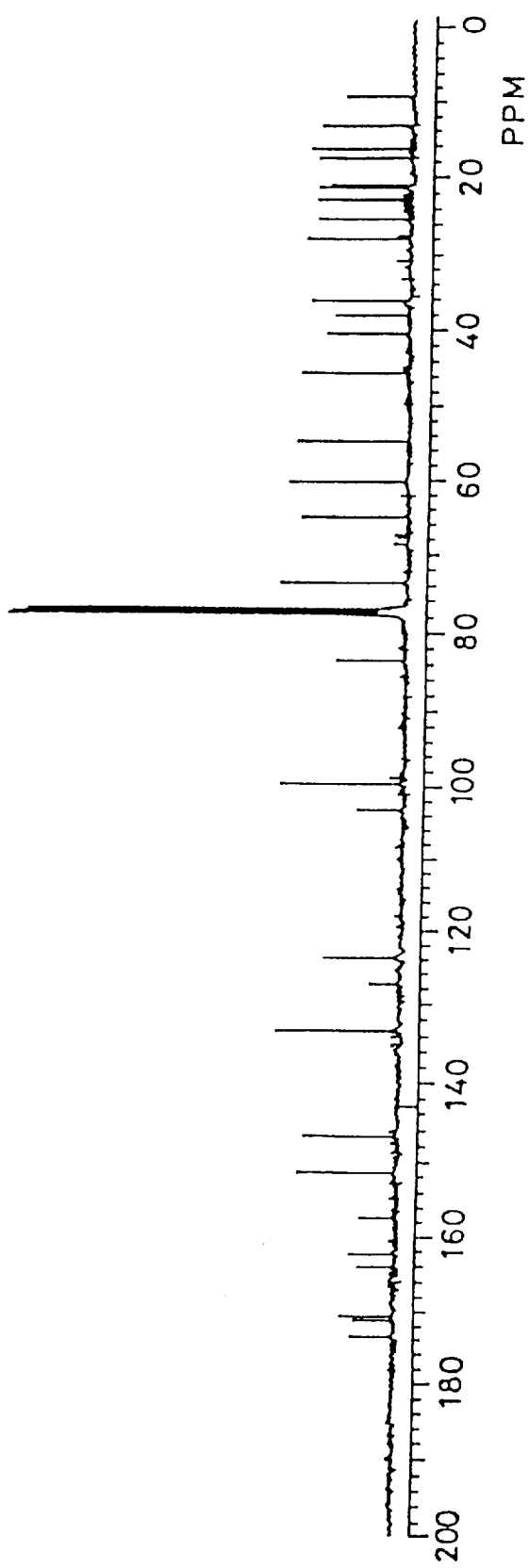
FIG. 12: $^{13}$C-NMR spectrum of FO-1289C substance.
Figure 13:
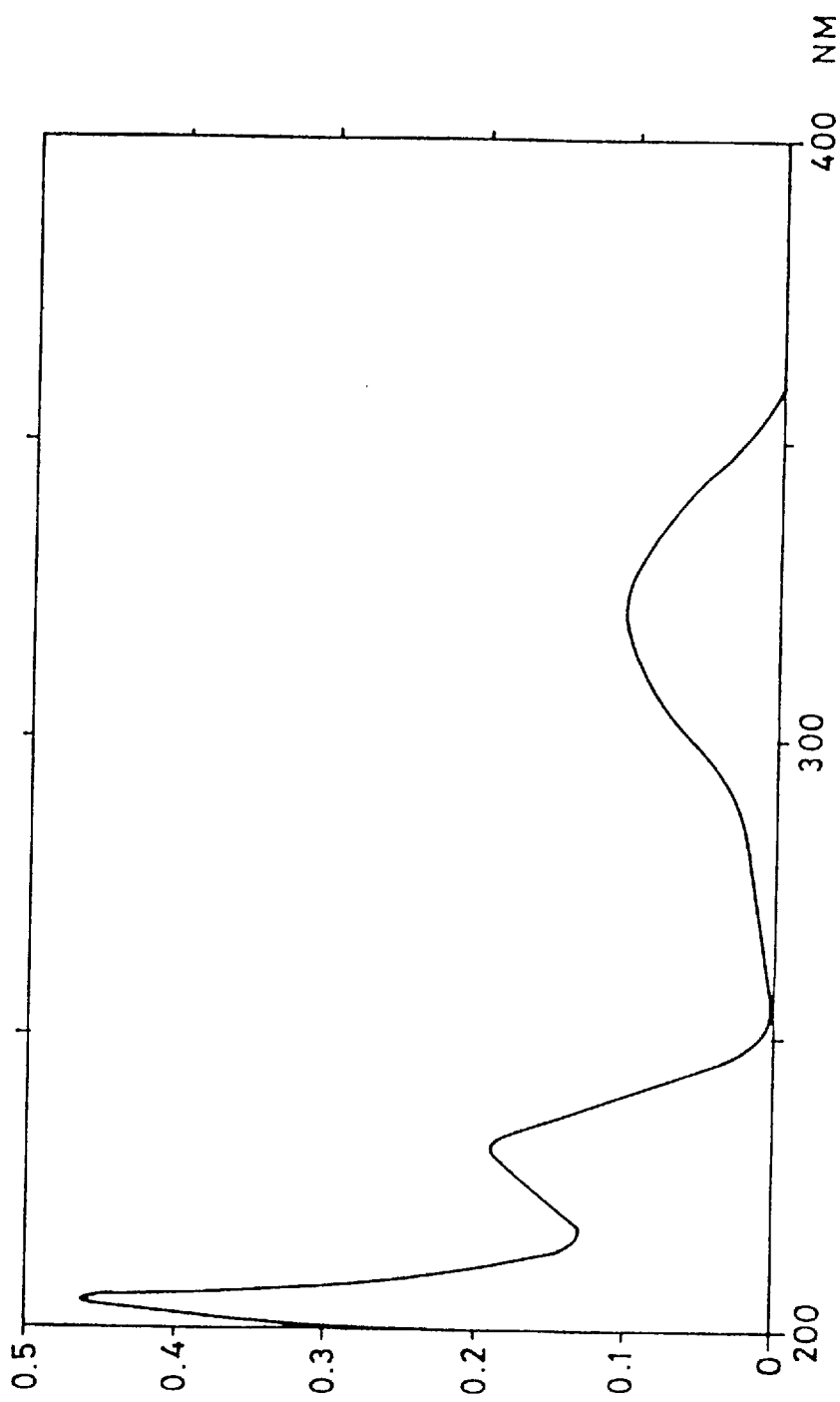
FIG. 13: UV spectrum of FO-1289D substance.
Figure 14:
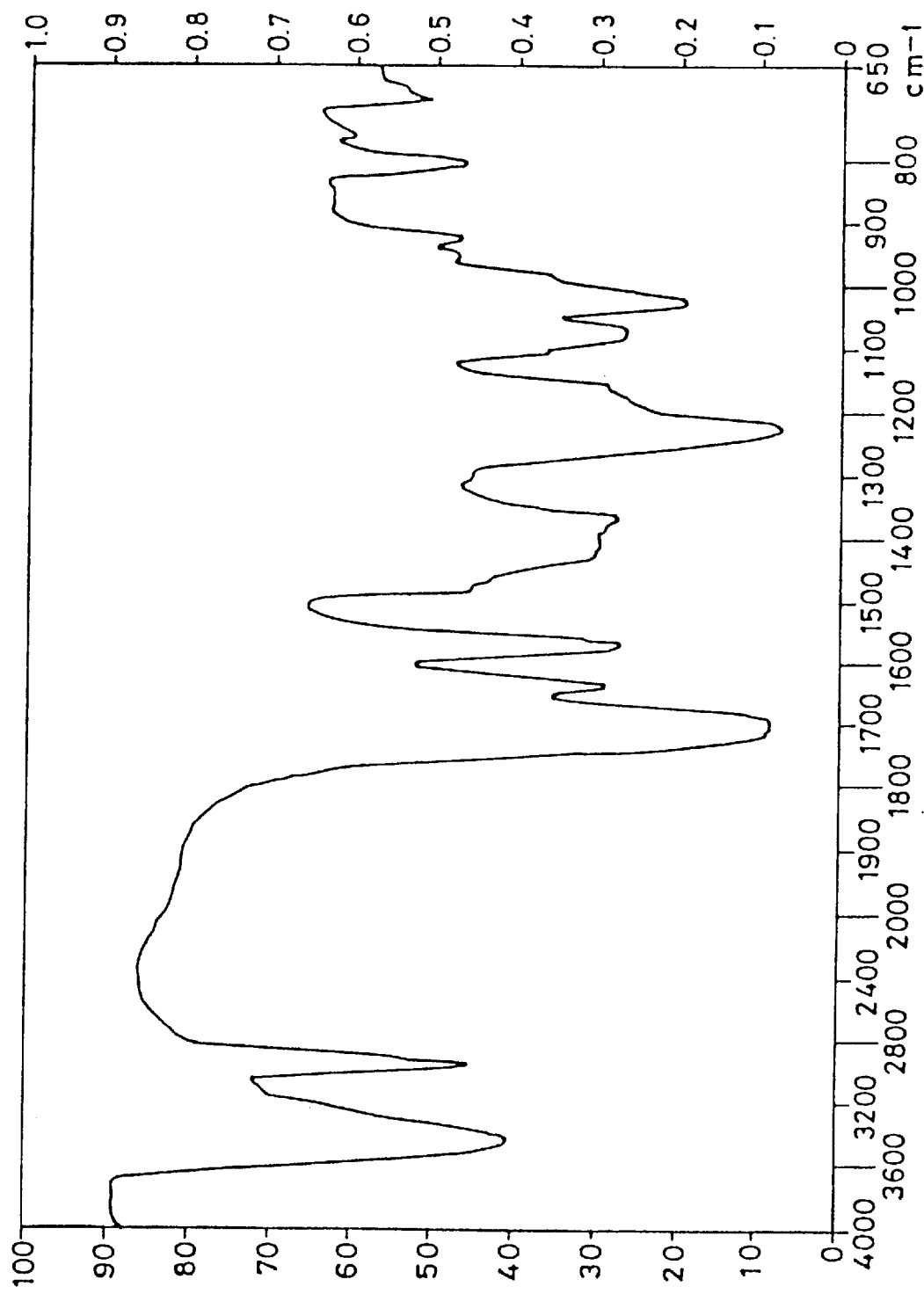
FIG. 14: IR spectrum of FO-1289D substance.
Figure 15:
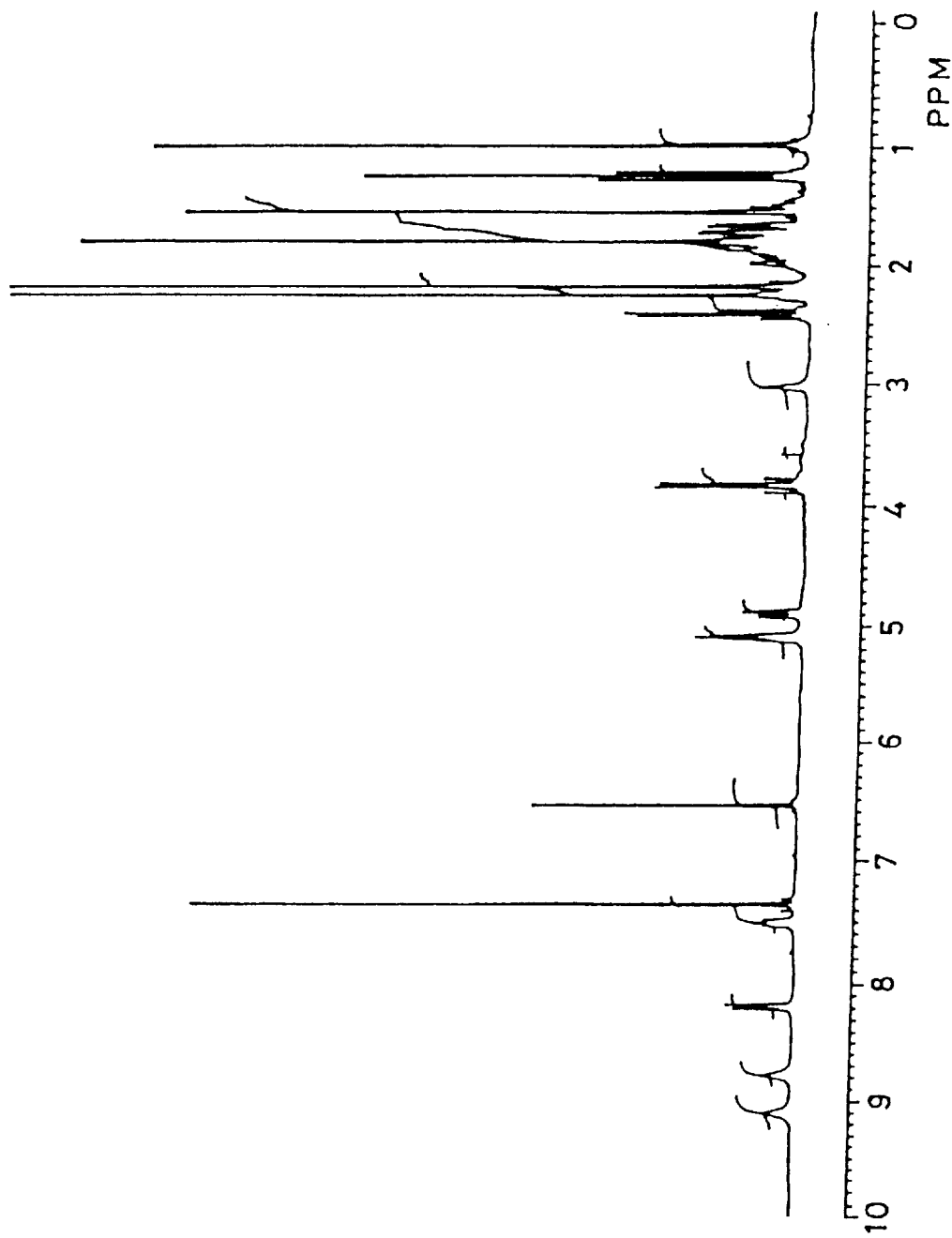
FIG. 15: $^1$H-NMR spectrum of FO-1289D substance.
Figure 16:
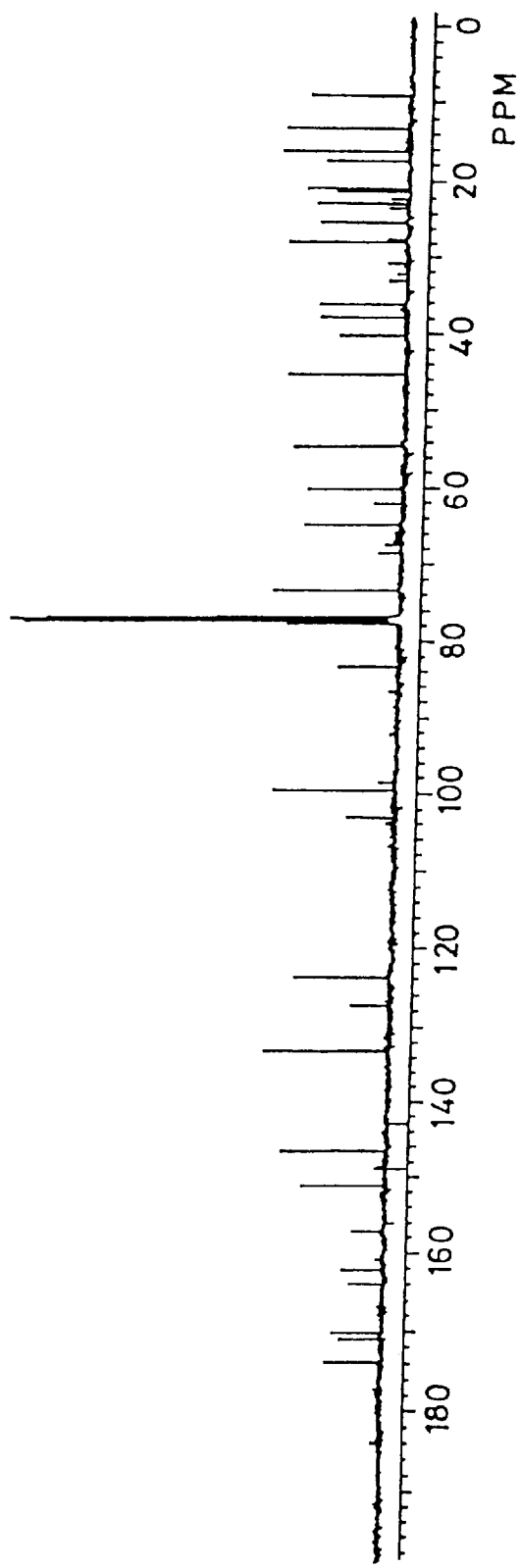
FIG. 16: $^3$C-NMR spectrum of FO-1289D substance.

Following example illustrates the present invention but is not construed as limiting.

EXAMPLE 1

A medium 100 ml (pH adjusted to 6.0) comprising glucose 2.0%, polypeptone 0.5%, yeast extract 0.2%, magnesium sulfate 0.05%, potassium dihydrogen phosphate 0.1% and agar 0.1% in 500 ml Erlenmeyer flask with cotton seal was steam sterilized. One loopful microorganism strain Aspergillus sp. FO-1289 FERM BP-4242 grown on a nutrient agar medium was inoculated into the medium and shake cultured at 27° C. for 48 hours to prepare seed culture liquid.

A medium comprising glucose 1.0%, Tripton 0.5%, yeast extract 0.3% and agar 0.3% (pH 6.0) in 50 lit. jar-fermenter was sterilized and cooled. The seed culture 200 ml was transferred aseptically thereto and the inoculated medium was cultured aerobically at agitation 250 rpm, aeration 10 lit./min. at 27° C. for 72 hours. Cultured liquid 30 lit. was extracted with ethyl acetate 18 lit. The extract was concentrated under reduced pressure to obtaine crude substance. The crude substance was charged on a column of silica gel (250 g. Merck, Art 9385) and eluted with a mixture of chloroform—methanol (99:1). Active fractions containing FO-1289 substance comprising each 100 ml fraction were collected and concentrated in vacuo to obtain the crude substance 1.5 g.

The crude substance was purified separately devided with 5 times by high performance liquid chromatography (Trirota V. Nihon Bunko Co., column YMC-Pack A-343. ODS resin. Yamamura Kagaku Kenkyusho) with solvent system 55% aqueous acetonitrile. detection UV 280 nm. flow rate 8 ml/min. The FO-1289A substance 50 mg, FO-1289B substance 5 mg, FO-1289C substance 5 mg and FO-1289D substance 4.5 mg were obtained.

We claim:

1. A process for production of FO-1289A, FO-1289B, FO-1289C and FO-1289D which comprises culturing Aspergillus sp. FERM BP-4242 in a nutrient medium, accumulating FO-1289A, FO-1289B, FO-1289C and FO-1289D in the medium, and isolating at least one of FO-1289A, FO-1289B, FO-1289C and FO-1289D therefrom.

2. A biologically pure culture of Aspergillus sp. FERM BP-4242.

3. A FO-1289A compound substance of the formula

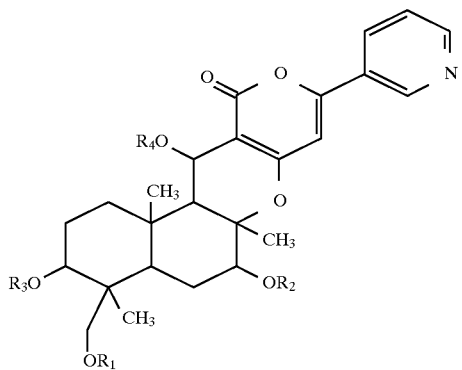

wherein $R_1$, $R_2$ and $R_3$ are acetyl and $R_4$ is hydrogen.

4. A FO-1289B substance of the formula

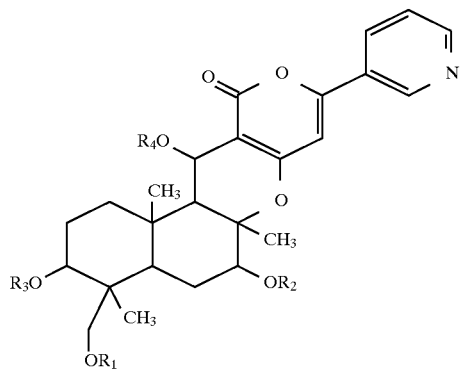

wherein $R_1$ is propionyl, $R_2$ and $R_3$ are acetyl and $R_4$ is hydrogen.

5. A FO-1289C compound of the formula

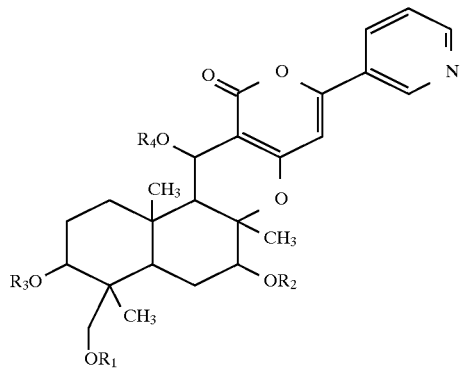

wherein $R_1$ and $R_3$ are acetyl, $R_2$ is propionyl and $R_4$ is hydrogen.

6. A FO-1289D compound of the formula

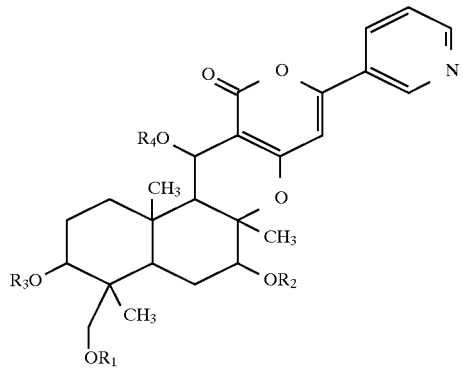

wherein $R_1$ and $R_2$ are acetyl, $R_3$ is propionyl and $R_4$ is hydrogen.

* * * * *